United States Patent [19]

Onoda et al.

[11] 4,146,574

[45] Mar. 27, 1979

[54] PROCESS FOR PREPARING HETEROPOLY-ACIDS

[75] Inventors: Takeru Onoda; Masayuki Otake, both of Yokohama, Japan

[73] Assignee: Mitsubishi Chemical Industries, Ltd., Tokyo, Japan

[21] Appl. No.: 797,771

[22] Filed: May 17, 1977

[30] Foreign Application Priority Data

May 17, 1976 [JP] Japan ................................. 51-56276

[51] Int. Cl.$^2$ ...................... C01B 25/00; C01B 15/16; C01B 25/26
[52] U.S. Cl. ...................................... 423/299; 423/306
[58] Field of Search ................ 423/299, 304, 305, 306

[56] References Cited

U.S. PATENT DOCUMENTS 3,227,518    1/1966    Kennedy ............................ 423/306

*Primary Examiner*—O. R. Vertiz
*Assistant Examiner*—Gregory A. Heller
*Attorney, Agent, or Firm*—Oblon, Fisher, Spivak, McClelland & Maier

[57] ABSTRACT

Heteropoly-acids suitable for use as a component of a variety of oxidation catalysts are prepared by hydrothermally reacting an aqueous slurry which contains an oxide and/or oxyacid each of molybdenum, vanadium and phosphorus and which may optionally contain an oxide and/or oxyacid of tungsten.

8 Claims, No Drawings

PROCESS FOR PREPARING HETEROPOLY-ACIDS

BACKGROUND OF THE INVENTION

1. Field of the Invention

This invention relates to a process for preparing heteropoly-acids and more particularly to a process for preparing a free heteropolyphosphoric acid containing molybdenum, vanadium and optionally tungsten as peripheral coordinate atoms. In one aspect this invention relates to a process for preparing a heteropoly-acid catalyst comprising such a heteropolyphosphoric acid supported on a carrier.

2. Description of the Prior Art

Heteropolyphosphoric acids are generally water-soluble substances having a structure in which oxy anions of peripheral coordinate atoms such as molybdenum, vanadium, tungsten, etc. are condensed about a phosphorus cation as the central element with a certain regularity. Those heteropolyphosphoric acids containing molybdenum and vanadium as peripheral coordinate atoms, that is, molybdovanadophosphoric acids, are useful as catalysts for oxidation, etc., but their synthesis involves some difficulties. Heretofore the following methods have been known for the synthesis of molybdovanadophosphoric acids.

(1) An aqueous slurry is prepared from an alkali vanadate, phosphoric acid and molybdic acid and heated. Thereafter hydrochloric acid is added and the mixture is extracted with ether; Zh. Obshch. Khim., 24, 966 (1954).

(2) Sulfuric acid is added to an aqueous solution of alkali vanadate, alkali phosphate and alkali molybdate and the mixture is then extracted with ether; Inorg. Chem., 7, 437 (1968).

While the above methods (1) and (2) are effective for reducing the time of reaction, it is necessary to use an alkali vanadate as the vanadium source or otherwise vanadium oxide must be homogeneously dissolved in an aqueous alkali solution prior to the condensation reaction. In addition, the vanadium source must be used in stoichiometrically large excess. These prior art methods are also disadvantageous in commercial operations, since the removal of the alkali residue requires complicated procedures involving strong acidification of the slurry or solution with excess mineral acid and subsequent extraction thereof with an organic solvent such as ether, as well as an additional step of treating the waste acid. In order to avoid these disadvantages, it has been proposed to calcine an intimate mixture consisting of a molybdenum compound, a vanadium compound and a phosphorus compound at an elevated temperature in an oxidizing atmosphere and subsequently extracting the mixture with water (Japanese Patent Laying-Open Publication No. 133,298/74). This method, however, has failed to completely solve the problem of the slow extraction rates involved therein.

Another method has been proposed which is directed to the preparation of alkali metal salts of molybdovanadophosphoric acids by heating an aqueous slurry containing an alkali vanadate, an alkali phosphate and molybdenum oxide, adding an alkali hydroxide to solubilize the solids in the slurry and then adding a mineral acid (British Pat. No. 1,376,432). This method, however, can not yield a free molybdovanadophosphoric acid which is effective as an oxidation catalyst.

SUMMARY OF THE INVENTION

It is therefore an object of this invention to provide a simple and practical process for the preparation of free molybdovanadophosphoric acids.

It is another object of this invention to provide heteropoly-acid catalysts comprising the same on a carrier, which are particularly effective for oxidation reactions.

These and other objects of this invention, as will hereinafter be made clear from the ensuing discussion can be attained by providing (1) a process for preparing a heteropoly-acid which comprises hydrothermally reacting an aqueous slurry which contains an oxide and/or oxyacid each of molybdenum, vanadium and phosphorus and which may optionally contain an oxide and/or oxyacid of tungsten, thereby forming an aqueous solution of a heteropolyphosphoric acid containing molybdenum and vanadium as peripheral coordinate atoms, a part of said molybdenum being optionally substituted by tungsten; and (2) a process for preparing a heteropoly-acid catalyst which comprises hydrothermally reacting an aqueous slurry which contains an oxide and/or oxyacid each of molybdenum, vanadium and phosphorus and which may optionally contain an oxide and/or oxyacid of tungsten, thereby forming an aqueous solution of a heteropolyphosphoric acid containing molybdenum and vanadium as peripheral coordinate atoms, a part of said molybdenum being optionally substituted by tungsten; and subsequently impregnating a carrier with the aqueous solution so as to have the heteropolyphosphoric acid supported on the carrier.

DESCRIPTION OF THE PREFERRED EMBODIMENTS

The heteropoly-acids which can be prepared according to this invention are those comprising phosphorus as the central element and molybdenum, vanadium and optionally tungsten as the peripheral coordinate atoms. Typically these heteropoly-acids may be represented by the general formula (A)

$$H_{3+x}Mo_{12-x-y}W_yV_xPO_{40} \cdot nH_2O \ldots \qquad (A)$$

wherein x is an integer of 1 to 4, y is an integer of 0 to 3, the sum of x+y is 1 to 4, and n represents the number of water of crystallization and usually has a value within the range of 16 to 32 in its crystalline state.

According to this invention, the raw materials used are oxides and/or oxyacids of molybdenum, vanadium, phosphorus and tungsten. Specific examples of suitable compounds of these to be used as the raw materials include molybdenum trioxide, molybdic acid; vanadium pentoxide, metavanadic acid; phosphoric acid, phosphorus pentoxide; tungsten trioxide, tungstic acid, and the like.

In preparing an aqueous slurry containing these raw materials, it is desirable to use them in proportions almost equal (up to 20% excess) to the stoichiometric proportions, that is, the proportions calculated from the composition of the desired heteropoly-acid.

The raw materials are preferably divided as finely as possible. For this purpose, molybdenum trioxide, vanadium pentoxide, etc., for example, are desirably pre-pulverized by ball milling or the like. More advantageously, a certain type of finely divided material may be used such as, for example, the molybdenum trioxide obtained by reacting molybdenite (molybdenum sulfide ore) in air and purifying the resulting crude molybdenum oxide by means of sublimation; the vanadium pentoxide obtained by roasting ammonium metavanadate in air, and the like. As the particle size is reduced, the particles become more advantageous with respect to reaction rate. If ultrafine particles which are inconvenient to transport or handling are used, it is preferred to add an appropriate amount of water to the particles. The hydrothermal reaction of the aqueous slurry may be carried out in a manner known per se, usually in an oxidizing atmosphere using air, oxygen, etc. The slurry concentration may be varied over a wide range. However, at an extremely low concentration, much energy is disadvantageously consumed in the subsequent concentration step of the reaction mixture, whereas at an extremely high concentration stirring of the slurry may be so hindered that the hydrothermal reaction rate is decreased. On this account it is preferable to adjust the weight ratio of oxides to water in the slurry approximately within the range of from 60/40 to 1/99. Temperature and pressure are usually in the range of 60° to 250° C. and atmospheric to 30 kg/cm$^2$, preferably in the range of 60° to 220° C. and atmospheric to 18 kg/cm$^2$. The reaction is continued until a large portion of the solids in the slurry dissolves. Since the rate of dissolution depends on the temperature and pressure and more largely on the particle size of the oxides, the reaction time cannot be fixed uniformly, although a period of 1 hour to 20 days is usually employed. Preferably, in order to accelerate the reaction rate, the aqueous slurry is thoroughly stirred. When the reaction is complete, the insoluble solids almost disappear and the resulting reaction liquor assumes a characteristic bright red color. After the reaction has been completed, the liquor is filtered to remove any insoluble residue, and a clear aqueous solution of the desired heteropolyphosphoric acid is obtained.

The aqueous solution thus obtained may be used for various applications as it is or after being diluted or concentrated to an appropriate concentration. When it is desired to isolate the free heteropolyphosphoric acid, the aqueous solution may be concentrated and then allowed to cool to provide the heteropolyphosphoric acid in crystal form.

While the free heteropolyphosphoric acid obtained in the above manner per se is useful as a catalyst for a variety of purposes, a heteropolyphosphoric acid catalyst supported on a carrier may readily be prepared by immersing the carrier in the aqueous solution of heteropolyphosphoric acid. The carrier may be any conventional carrier which can be used in commercial operation, although in particular highly siliceous compounds such as, for example, silica, silica sol and diatomaceous earth are preferred. Since diatomaceous earth usually occurs in powder form, it is preferable to use it in granular or pellet form having a high mechanical strength. In addition, in order to enhance the catalytic activity of the heteropolyphosphoric acid any suitable element may be added as a second component, as required. For this purpose, the heteropolyphosphoric acid and a compound of the above element may be supported simultaneously or successively on the carrier, which is then dried and, if necessary, calcined in air to obtain the desired catalyst.

When the catalyst is to be used for oxidation, the second component is selected from the compounds of Group I to VIII elements in the periodic table, more specifically those compounds listed in Table 1 below.

Table 1

| Group | Element | In the Form of |
|---|---|---|
| I | Li, Na, K, Rb, Cs, Cu | |
| II | Mg, Zn, Cd | nitrate, sulfate, carbonate, phosphate, oxide, heteropoly-acid salt, fluoride, chloride, bromide |
| III | In, Tl | |
| IV | Zr, Pb, Sn | |
| V | V, Bi | oxide, nitrate, molybdate |
| VI | Mo, Cr, Te | oxide, oxyacid, nitrate |
| VII | F, Cl, Br, I | Group I metal salt |
| VIII | Fe, Co, Ni | oxide, sulfate, molybdate |

The second component is added usually to the heteropolyphosphoric acid in a molar ratio of not greater than 10.

The heteropolyphosphoric acid catalyst obtained in accordance with the present invention may be primarily used for oxidation reaction. It may also be used in a number of organic reactions known to be acid-catalyzed, such as the hydration of olefins, esterification, isomerization and the like as well, since it has increased solid acidity as compared with prior art catalysts comprising the same or similar elements. The term "oxidation" as used herein is intended to refer broadly to any organic reaction between molecular oxygen and a reaction substrate which causes addition of oxygen to the substrate and/or oxidative dehydrogenation therefrom, and specifically includes, for example, those reactions from isobutyric acid to methacrylic acid, from isobutyrate to methacrylate, from isobutyraldehyde to methacrolein and methacrylic acid, from methacrolein to methacrylic acid, from isobutylene to methacrolein and methacrylic acid, from butene to maleic anhydride, from methyl isopropyl ketone to methyl isopropenyl ketone, etc.

As described in detail above, in accordance with this invention, the free heteropolyphosphoric acid can be readily and economically prepared in high yield from molybdenum, vanadium, phosphorus and tungsten compounds in stoichiometric ratios calculated from the composition of the desired heteropolyphosphoric acid product. In addition, a highly active, stable catalyst having excellent reproducibility can be prepared from the heteropolyphosphoric acid.

Having generally described this invention, a more complete understanding can be obtained by reference to certain examples which are provided herein for purpose of illustration only and are not intended to be limiting in any manner.

EXAMPLE 1

Three hundred and sixty (360) grams of molybdenum trioxide (technical grade purified by sublimation; finely divided), 63.8 g of vanadium pentoxide (finely divided) and 28.8 g of phosphoric acid (85%, GR) were weighed and mixed with 2 l of water to provide a yellowish orange slurry which contained the starting materials in the atomic ratio of Mo/V/P of 10/2.4/1. The slurry was then placed in a flask fitted with a reflux condenser and heated to boil (at 104° C.) over about 2 hours on a heating mantle while stirring by passing water-scrubbed air through the slurry. After the boiling had been continued under these conditions for 20 days, the liquor turned bright red and a large portion of the solids was dissolved. The resulting liquor was filtered through a quantitative filter paper (Toyo Filter Paper No. 5B) to filter out the insoluble residue and obtain an aqueous solution of heteropolyphosphoric acid. The aqueous solution was concentrated to 300 ml in a rotary evaporator and then allowed to stand at room temperature resulting in the growth of deep red macrocrystals. These crystals were identified as free 10-molybdo-2-vandophosphoric acid by X-ray spectroscopy. Elementary analysis after recrystallization from water gave the atomic ratio of Mo/V/P of 10/2.0/1.0, which was in agreement with the theoretical value for $H_5Mo_{10}V_2PO_{40}$.

Quantitative analysis of the insoluble residue according to conventional manner showed that its total weight was 11.26 g of which $V_2O_5$ comprised at least 98%. Hence the insoluble residue from the hydrothermal reaction can be used as a vanadium source in the subsequent batch for the synthesis of heteropolyphosphoric acid.

EXAMPLE 2

To 288 g of commercially available molybdenum trioxide (Kishida Kagaku, GR, highly crystalline) and 43.6 g of vanadium pentoxide (ditto) was added 80 ml of water, and the mixture was ball milled for an hour before 560 ml of water and 23.0 g of 85% phosphoric acid were added. The resulting yellowish orange slurry which contained the raw materials in the atomic ratio of Mo/V/P of 10/2.4/1 was placed in a flask fitted with a reflux condenser and heated to reflux in an oil bath for 20 days, during which time it turned bright red and a large portion of the solids was dissolved. The liquor was concentrated to 200 ml, then filtered through a quantitative filter paper (Toyo Filter Paper No. 5C) to separate the insoluble residue and allowed to cool, resulting in the growth of deep red macrocrystals. The macrocrystals were identified as 10-molybdo-2-vanadophosphoric acid, as in Example 1, by means of X-ray spectroscopy.

A quantitative yield of the crystals was obtained. The insoluble residue, when subjected to conventional quantitative analysis, had a total weight of 7.2 g of which vanadium pentoxide comprised 99%. Hence the insoluble residue from the hydrothermal reaction in this example can be used directly as a vanadium source in the subsequent batch for the synthesis of heteropolyphosphoric acid.

EXAMPLE 3

Following the procedures as described in Example 1 except that the aqueous solution from which the insoluble residue had been filtered off was concentrated to 600 ml, an aqueous heteropolyphosphoric acid solution was obtained, which was used in the preparation of catalysts in the following examples.

EXAMPLE 4

In 10 ml of the aqueous heteropolyphosphoric acid solution prepared in Example 3, 3 g of granulated diatomaceous earth carrier was immersed to support the heteropolyphosphoric acid thereon and then dried. The thus obtained catalyst is hereinafter referred to as Catalyst 1.

EXAMPLE 5

In an aqueous solution of 35.4 mg of ammonium paramolybdate in 2 ml of water was immersed 2 g of granulated diatomaceous earth carrier which had been sieved to 24 to 40 mesh. The impregnated carrier was then dried and calcined in air at 400° C. for 2 hours. The calcined product contained molybdenum trioxide as a second component in an amount of 0.1 m mole as molybdenum atom per gram of the carrier. Subsequently, it was immersed in 2 ml of the aqueous heteropolyphosphoric acid prepared in Example 3. The catalyst obtained after drying is hereinafter referred to as Catalyst 2.

EXAMPLE 6

Following the procedures described in Example 5, 2 g of the granulated diatomaceous earth carrier was immersed in a mixture of 1 ml of 0.05 M vanadyl oxalate and 1 ml of water, then dried and calcined. The calcined product contained vanadium pentoxide as a second component in an amount of 0.05 m mol as vanadium atom per gram of the carrier. It was further immersed in 2 ml of the aqueous heteropolyphosphoric acid solution prepared in Example 3, and dried to provide a catalyst which is hereinafter referred to as Catalyst 3.

EXAMPLE 7

Following the procedures described in Example 5, various heteropolyphosphoric acid catalysts were prepared which contained a wide variety of second components as shown in Table 2.

Table 2

| Catalyst No. | Second Component Source | Form on Carrier | Amount of Second Component (MMol Metal Element/G Carrier) |
|---|---|---|---|
| 4 | $Cu(NO_3)_2$ | CuO | 0.1 |
| 5 | $CuBr_2$ | $CuBr_2$ | 0.1 |
| 6 | $Cu(NO_3)_2$ | CuO | 0.1 |
|  | $Li_2SO_4$ | $Li_2SO_4$ | 0.05 |
| 7 | $CrO_3$ | $CrO_3$ | 0.1 |
| 8 | $Cr(NO_3)_3$ | $Cr_2O_3$ | 0.05 |
| 9 | $Cd(NO_3)_2$ | CdO | 0.1 |
| 10 | $UO_2(NO_3)_2$ | $U_3O_8$ | 0.1 |
| 11 | $In(NO_3)_3$ | $In_2O_3$ | 0.05 |
| 12 | $La(NO_3)_3$ | $La_2O_3$ | 0.05 |
| 13 *1 | $H_6TeO_6$ | $H_6TeO_6$ | 0.1 |
| 14 | $Tl(NO_3)_3$ | $Tl_2O_3$ | 0.1 |
| 15 | $NiSO_4$ | $NiSO_4$ | 0.1 |
| 16 | $Mg(NO_3)_2$ | MgO | 0.05 |
|  | $Cr(NO_3)_3$ | $Cr_2O_3$ | 0.05 |
| 17 | $Co(NO_3)_2$ | CoO | 0.05 |
|  | $Cr(NO_3)_3$ | 0.05 |  |
| 18 | $Zr(NO_3)_4$ | $ZrO_2$ | 0.1 |

*1 Not calcined

EXAMPLE 8

A 200 ml titanium-lined autoclave was charged with 18.0 g of molybdenum trioxide the same as that used in Example 1, 3.19 g of vanadium pentoxide, 1.44 g of phosphoric acid (85%, GR) and 100 g of water. The autoclave was heated to a temperature of 200° C. and a pressure of 15.4 kg/cm$^2$, and the reaction was carried out for 11 hours with vigorous stirring (700 rpm) of the reaction mixture.

The resulting liquor was filtered and the filtrate concentrated to give the deep red crystals.

The yield of the crystal was nearly quantitative.

EXAMPLE 9

To a 500 ml flask fitted with a reflux condenser, an agitator and a thermometer was added a yellowish orange slurry of 14.40 g of molybdenum trioxide the same as that used in Example 1, 1.819 g of vanadium pentoxide (Nichia Kagaku Co., Ltd., technical grade powder, average particle size: 1.5 $\mu$) and 1.140 g of phosphoric acid (85%, GR) in 320 ml of water having an atomic ratio of 10 Mo/2V/1P.

The slurry was heated at 90° C. for 20 hours. At the end of this period, the reaction mixture was filtered to remove a trace amount (ca. 20 mg) of the insoluble residue. The filtrate was concentrated to give the deep red crystals of free $H_5Mo_{10}V_2PO_{40}$.

EXAMPLE 10

To a 1 l flask fitted with a reflux condenser, an agitator and a thermometer was added a slurry of 20.15 g of molybdenum trioxide the same as that used in Example 1, 2.57 g of vanadium pentoxide (Kishida Kagaku Co., Ltd., GR, highly crystalline) ball-milled with 30 ml of water for an hour, and 1.29 g of phosphoric acid (85%, GR) in 1,000 ml of water having an atomic ratio of 10 Mo/2V/0.8P.

The slurry was heated at 104° C. for 3 hours and then at a temperature between 60° C. and 70° C. for additional 40 hours. At the end of this period, the reaction mixture was filtered to remove 5.7 g of the insoluble residue. Concentration of the filtrate gave a heteropolyphosphoric acid crystal in a 94.7% yield based on the stoichiometry of phosphoric acid.

Application 1 (Oxidative dehydrogenation of isobutyric acid)

Catalysts 1 to 18 prepared in Examples 4 to 7 were tested for oxidative dehydrogenation of isobutyric acid. The reaction was carried out in a vertical hard glass reaction tube equipped with gas inlet and outlet and the product was analyzed by means of acidimetry, gas chromatography and the like. The reaction conditions were:
Starting gas: Insobutyric acid/Steam/Oxygen/Nitrogen = 2/4/3/91 (mol %)
Space velocity (GHSV): 5,000
Reaction temperature: 310° C.
The results are summarized in Table 3.

Table 3

| Catalyst No. | % Conversion of Isobutyric Acid | % Selectivity Toward Methacrylic Acid |
| --- | --- | --- |
| 1 | 98.0 | 67.2 |
| 2 | 100.0 | 70.5 |
| 3 | 100.0 | 73.4 |
| 4 | 99.0 | 71.8 |
| 5 | 100.0 | 71.1 |
| 6 | 100.0 | 74.8 |
| 7 | 100.0 | 69.2 |
| 8 | 100.0 | 70.0 |
| 9 | 98.0 | 70.5 |
| 10 | 100.0 | 71.2 |
| 11 | 94.5 | 71.1 |
| 12 | 98.0 | 73.4 |
| 13 | 81.0 | 70.0 |
| 14 | 93.0 | 70.8 |
| 15 | 81.0 | 70.0 |
| 16 | 70.0 | 71.3 |
| 17 | 97.0 | 72.0 |
| 18 | 91.9 | 75.6 |

Application 2 (Oxidative dehydrogenation of methyl isobutyrate)

A mixed gas of methyl isobutyrate, oxygen and nitrogen was introduced into a reaction tube packed with 15 ml of Catalyst 1. The reaction tube is the same as in Application 1, and the reaction conditions were:
Starting gas: Methyl isobutyrate/Oxygen/Nitrogen = 3.2/2.7/94.1 (mol %)
Space velocity (GHSV): 1,000
Reaction Temperature: 280° C.
The results are summarized in Table 4.

Table 4

| % Conversion of Methyl Isobutyrate | 58.1% |
| --- | --- |
| % Selectivity Toward Methyl Methacrylate (I) | 45.1% |
| % Selectivity Toward Methacrylic Acid (II) | 38.8% |
| (I) + (II) | 83.9% |

Application 3 (Oxidative dehydrogenation of isobutyraldehyde)

A mixed gas of isobutyraldehyde, oxygen and nitrogen was introduced in a reaction tube packed with 15 ml of Catalyst 1. The reaction tube was the same as in Application 1 and the reaction conditions were set as follows:
Starting gas: Isobutyraldehyde/Oxygen/Nitrogen = 4.7/12.7/82 (mol %)
Space velocity (GHSV): 1,000
Reaction Temperature: 290° C.
The results are summarized in Table 5.

Table 5

| % Conversion of Isobutyraldehyde | 93.6% |
| --- | --- |
| % Selectivity Toward Methacrolein | 72.6% |
| % Selectivity Toward Methacrylic Acid | 6.2% |

Application 4 (Oxidation of methacrolein)

A mixed gas consisting essentially of 4% by volume of methacrolein, 5% of oxygen, 25% of steam and 66% of nitrogen was reacted by introducing it into a reaction tube packed with Catalyst 1. The results obtained at a space velocity (GHSV) of 1,000 and a reaction temperature of 320° C. are summarized in Table 6.

Table 6

| % Conversion of Methacrolein | 60% |
| --- | --- |
| % Selectivity Toward Methacrylic Acid | 57% |

Application 5 (Oxidative dehydrogenation of methyl isopropyl ketone)

A mixed gas of methyl isopropyl ketone, water, oxygen and nitrogen was introduced in a reaction tube packed with 2.0 ml of Catalyst 1. The reaction tube was the same as in Application 1 and the substrate feed rate was set as follows:

| Methyl isopropyl ketone | 10.9 m mol/hr |
| --- | --- |
| $H_2O$ | 52.8 |
| $O_2$ | 15.0 |
| $N_2$ | 234.9 |

The reaction was carried out at temperatures of 265° C. and 285° C.
The results are summarized in Table 7.

Table 7

|  | at 265° C | at 285° C |
| --- | --- | --- |
| % Conversion of Methyl Isopropyl Ketone | 54.3% | 83.2% |
| % Selectivity Toward Methyl Isopropenyl Ketone | 73.2% | 84.5% |

What is claimed as new and intended to be covered by Letters Patent is:

1. A method for preparing a heteropoly acid, which comprises: hydrothermally reacting an oxide, ocyacid or mixtures thereof of molybdenum, vanadium and phosphorus in an aqueous slurry such that said reaction is conducted at a temperature of 60° to 250° C. under a pressure ranging from atmospheric to 30 kg/cm² which permit an aqueous solution of a heteropolyphosphoric acid containing molybdenum and vanadium as peripheral coordinate atoms to form, said molybdenum, vanadium and phosphorus slurry components being present in said slurry in amounts from about equal to up to 20% in excess of the stoichiometric amount for each component of the heteropoly acid desired.

2. The method of claim 1, wherein a portion of said molybdenum component is substituted by tungsten.

3. The method of claim 1, wherein said molybdenum, vanadium and phosphorus components are present in said slurry in amounts substantially equal to the portions necessary for the synthesis of a desired heteropolyphosphoric acid.

4. The method of claim 1, wherein the weight ratio of molybdenum, phosphorus and vanadium components to water ranges from 60/40 to 1/99.

5. The process according to claim 1, wherein the heteropolyphosphoric acid is crystallized from the aqueous solution obtained.

6. The method of claim 1, wherein said molybdenum component is $MoO_3$ or molybdic acid, said vanadium component is $V_2O_5$ or metavanadic acid and said phosphorus component is phosphoric acid or $P_2O_5$.

7. The method of claim 1, wherein said hydrothermal reaction is conducted under an oxidizing atmosphere.

8. The method of claim 7, wherein said oxidizing atmosphere is air.